(12) United States Patent
Gayed

(10) Patent No.: US 7,109,161 B1
(45) Date of Patent: Sep. 19, 2006

(54) PRESERVED PHARMACEUTICAL FORMULATIONS

(75) Inventor: Atef Gayed, Overland Park, KS (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 450 days.

(21) Appl. No.: 10/031,922

(22) PCT Filed: Jul. 21, 2000

(86) PCT No.: PCT/US00/20040

§ 371 (c)(1),
(2), (4) Date: May 13, 2002

(87) PCT Pub. No.: WO01/07086

PCT Pub. Date: Feb. 1, 2001

Related U.S. Application Data

(60) Provisional application No. 60/228,815, filed on Jul. 22, 1999.

(51) Int. Cl.
*A61K 38/00* (2006.01)
*A61K 31/70* (2006.01)
*A61K 31/554* (2006.01)
*A61K 31/501* (2006.01)
*A61K 31/44* (2006.01)

(52) U.S. Cl. ................ 514/2; 514/27; 514/211.07; 514/252.01; 514/282; 514/643; 514/717; 424/94.6

(58) Field of Classification Search .............. 424/94.6; 514/2, 27, 211.07, 252.01, 282, 643, 717
See application file for complete search history.

(56) References Cited

U.S. PATENT DOCUMENTS

| | | | |
|---|---|---|---|
| 3,489,837 A | 1/1970 | Hyman | ................ 424/257 |
| 4,053,628 A | 10/1977 | Stevenson et al. | ......... 424/283 |
| 4,377,513 A | 3/1983 | Sugimoto et al. | |
| 4,506,018 A | 3/1985 | North, Jr. | ................ 436/10 |
| 4,703,008 A | 10/1987 | Lin | |
| 4,806,524 A | 2/1989 | Kawaguchi et al. | |
| 5,045,529 A | 9/1991 | Chiang | ................ 514/6 |
| 5,503,827 A | 4/1996 | Woog et al. | |
| 5,597,560 A | 1/1997 | Bergamini et al. | ....... 424/78.04 |
| 5,661,125 A | 8/1997 | Strickland | |
| 5,863,562 A | 1/1999 | Tsao et al. | ................ 424/616 |
| 6,022,551 A | 2/2000 | Jampani et al. | ............ 424/405 |

FOREIGN PATENT DOCUMENTS

| | | |
|---|---|---|
| EP | 0 199 992 | 11/1986 |
| EP | 0 459 795 | 5/1991 |
| EP | 0 930 065 | 7/1999 |
| WO | 01/07075 | 2/2001 |
| WO | 01/07086 | 2/2001 |

OTHER PUBLICATIONS

*Drug Facts and Comparisons 2000*, 54th ed., pp. 698, 1319, 1330.
*Merck Index*, 11th ed., pp. 7228 and 1084 (1989).
U.S. Appl. No. 10/031,947, entitled "Multi-Dose Erythropoietin Formulations" by Atef Gayed filed May 15, 2002.
International Search Report dated Nov. 10, 2000.
Miyake, et al., "Purification of Human Erythropoietin," *J. Biol. Chem.*, 252(15):5558-67 (1997).
Sherwood, et al., "Erythropoietin Production by Human Renal Carcinoma Cells in Culture," *Endocrinology*, 99(2):504-10 (1976).
Sherwood, et al., "Establishment of Human Erythropoietin-Producing Renal Carcinoma Cell Line," *Clinical Research*, 31:323A (1983).
Durieux, Marcel E., M.D., "Synergistic Inhibition of Muscarinic Signaling by Ketamine Stereoisomers and the Preservative Benzethonium Chloride," *Anesthesiology* 86:1326-33 (1997).

*Primary Examiner*—Raymond J. Henley, III
(74) *Attorney, Agent, or Firm*—Vinson & Elkins L.L.P.

(57) ABSTRACT

The present invention is directed to the use of benzethonium chloride, alone or in combination with phenoxyethanol or phenyl ethyl alcohol, to provide anti-microbial activity in pharmaceutical compositions. The present invention also provides methods of using benzethonium chloride, alone or in combination with phenoxyethanol or phenyl ethyl alcohol, to inhibit microbial growth in pharmaceutical compositions.

45 Claims, No Drawings

PRESERVED PHARMACEUTICAL FORMULATIONS

This application is a 371 of PCT/US00/20040, filed Jul. 21, 2000, which claims benefit of U.S. Provisional Application No. 60/228,815, filed Jul. 22, 1999.

I. DESCRIPTION OF THE INVENTION

The present invention relates generally to the use of preservatives in multi-dose pharmaceutical formulations. More specifically, the present invention relates to the use of benzethonium chloride alone or in combination with phenoxyethanol or phenyl ethyl alcohol, in multi-dose pharmaceutical formulations comprising a variety of pharmacologically active ingredients.

II. BACKGROUND OF THE INVENTION

Sterility is one of the most important characteristics of pharmaceutical compositions. Maintenance of sterility of pharmaceutical compositions is a function of both the method of sterilization and the integrity of the packaging or application system. For products that are intended for multiple dosing, antimicrobial agents must be added to the product formulation to protect the product from accidental microbial contamination during its storage or use or both. This is true regardless of the dosage form of the composition.

Stable multi-dose pharmaceutical formulations containing a variety of active ingredients are viewed by the pharmaceutical industry as particularly advantageous and commercially attractive. These formulations are generally, though not always, are packaged in a manner that allows for the extraction of partial amounts of the formulation at various times. This type of system is desirable as it allows multiple doses to be obtained from a single container, and allows for more controlled administration of the pharmaceutical composition as the formulation may be withdrawn and used, applied or administered in any partial amount, and over an extended period of time.

The nature of the use of multi-dose formulations imposes special requirements on the formulation. For example, maintenance of the sterility of a composition is particularly challenging given the many opportunities for introduction of microorganisms and other contaminants into the formulations. Repeated introduction of foreign elements, for example, needles or swabs, into the multi-dose container after formulation also creates a likelihood of introducing microorganisms into the container. Additionally and alternatively, microorganisms may be introduced during filling of the containers or during reconstitution of the formulations after lyophilization and prior to use, application or administration. The extended periods of time over which the container may be stored—especially during multiple introductions of foreign elements, and/or after contaminants may have been introduced, demands that the formulation contain special additives to insure the sterility of the contents.

To insure that these formulations maintain optimally sterile properties, the United States Food and Drug Administration (USFDA) and regulatory agencies in other jurisdictions including in Europe and Japan, require that all multi-dose compositions contain preservatives to prevent the growth of, or to affirmatively kill, any microorganisms that may be introduced into them. The development of preservative-containing multi-dose formulations is challenging, however, because various active ingredients in pharmaceutical compositions tend to interact adversely with preservative compounds.

Possible adverse interactions between preservatives and pharmacologically active ingredients include the degradation of the active ingredients, especially ones stored for extended periods of time; inactivation, neutralization, or alteration of the active ingredients; formation of aggregates comprising the active ingredients and other additives or constituents of the formulations; and other interactions that inactivate, degrade or make the administration of the formulation to humans, by any dosage route, difficult, painful or otherwise undesirable.

Additionally, preservatives themselves are noted for causing acute adverse reactions, such as allergic reactions or even seizures, in humans upon administration. Ideally, a preservative contained in a multi-dose pharmaceutical formulation should be effective in low concentration against a wide variety of microorganisms; soluble in the formulation; non-toxic; compatible and nonreactive with the active ingredient as well as other additives; active with long term stability; and nonreactive with components of the container or closure system.

Sandeep Nema et al. published lists of various excipients that have been included in the formulation of injectable products marketed in the United States. The antimicrobial preservatives listed in this review article are included in Table 1:

TABLE 1

| ANTIMICROBIAL PRESERVATIVES | | |
| --- | --- | --- |
| Preservative | Frequency | Range |
| Benzalkonium chloride | 1 | 0.02% w/v |
| Benzethonium chloride | 4 | 0.01% |
| Benzyl alcohol | 74 | 0.75–5% |
| Chlorobutanol | 17 | 0.25–0.5% |
| m-cresol | 3 | 0.1–0.3% |
| Myristyl gamma-picolinium chloride | 2 | 0.0195–0.169% |
| Paraben methyl | 50 | 0.05–0.18% |
| Paraben propyl | 40 | 0.01–0.1% |
| Phenol | 48 | 0.2–0.5% |
| 2-Phenoxyethanol | 3 | 0.50% |
| Phenyl mercuric nitrate | 3 | 0.001% |
| Thimerosal | 46 | 0.003–0.01% |

Despite the range of preserving agents available, finding a reliable, broadly non-reactive preservative or combination of preservatives useful in pharmaceutical compositions remains elusive. Accordingly, there remains a need for a preservative or combination of preservatives that is minimally reactive with active ingredients in pharmaceutical formulations; is minimally reactive with other additives commonly used in multi-dose pharmaceutical formulations; maintains the stability of the active ingredient and the composition over an extended shelf life of the product; meets the United States, European, and Japanese pharmacopia criteria for preservative challenge testing; is safe in the concentrations used; and is administrable—by any parenteral, topical, ocular, inhaled or oral route—in a manner that is effective, and minimizes pain and the chance of adverse reaction, for example, allergic reaction in the patient.

III. SUMMARY OF THE INVENTION

The present invention provides novel and particularly advantageous multi-dose pharmaceutical formulations containing a variety of active pharmaceutical ingredients and the preservative benzethonium chloride alone or in combination with either phenoxyethanol or phenylethyl alcohol. Also provided are multi-dose pharmaceutical formulations containing a wide range of active ingredients and benzethonium chloride in combination with either phenoxyethanol or phenylethyl alcohol. Virtually any pharmacologically active ingredient may be employed. In all embodiments of the present invention, those ingredients specifically contemplated to be useful in the present invention include agents used to treat the cardiovascular and gastrointestinal systems as well as the liver. Additional agents contemplated to be within the scope of the present invention include topical, hematologic, antihistaminic, antimicrobial, antiepileptic and anti-seizure agents as well as agents used as sedatives, hypnotics, diuretics, psychopharmacologics, anti-migraine agents, hormones, proteins or peptides or any other active ingredient. These active agents may be used alone or in combination and remain within the scope of the present invention. In particularly preferred embodiments, one or more active ingredient is included in a pharmaceutical composition containing benzethonium chloride in combination with phenoxyethanol, as these two preservatives display a synergistic anti-microbial effect.

In addition to embodiments comprising the active agent as outlined above, an alternative embodiment of the present invention provides a pharmaceutical carrier composition comprising any of the pharmaceutically active ingredients listed above, as well as an amount of benzethonium chloride, or any of the active ingredients as well as benzethonium chloride in combination with either phenoxyethanol or phenylethyl alcohol.

In another preferred embodiment, the present invention provides a vial or pharmaceutical package for containing any pharmacologically active ingredient preserved with an effective amount of benzethonium chloride alone, or an effective amount of benzethonium chloride in combination with phenoxyethanol or phenylethyl alcohol.

Still other preferred embodiments of the present invention are methods for inhibiting microbial growth in compositions including one or more pharmacologically active agents. These methods include adding to the active ingredient or combination of active ingredients, the preservative benzethonium chloride alone, or in combination with either phenoxyethanol or phenylethyl alcohol.

IV. DETAILED DESCRIPTION OF THE INVENTION

The present invention provides a significant improvement over the state of the art. Provided are multi-dose pharmaceutical formulations containing a wide range of active ingredients as well as the preservative benzethonium chloride alone, or in combination with either phenoxyethanol or phenylethyl alcohol. The disclosed compositions are stable, sterile and easily administered. Further, and most unexpectedly, the present invention discloses that phenoxyethanol and benzethonium chloride, when used in combination in a multi-dose pharmaceutical composition, have positive synergistic effects resulting in a particularly advantageous composition. Specifically, this combination of preservatives displays the following characteristics: (1) synergistic antimicrobial effect, allowing for a lower concentration of preservatives to be used; (2) excellent compatibility with the active ingredients in various pharmaceutical formulations, at varying storage conditions, over extended periods of time and over a broad range of pHs; and (3) phenoxyethanol has a potential for a local anesthetic effect, making the composition particularly preferable for subcutaneous administration.

The preserved pharmaceutical compositions disclosed in the present invention may be embodied in virtually any form of dosing, and may be administered via virtually any route of administration. Exemplary useful dosage forms include but are not limited to a liquid, suspension, emulsion, solution, mixture, cream, ointment, gel, oil, suppository, semi-solid, aerosol, powder, tablet or capsule. Exemplary routes of administration of the preserved pharmaceutical compositions disclosed herein include parenteral, via mucosa, ocular, aural, oral, topical, by suppository and by inhalation.

As used herein, the following terms have the following meanings:

Pharmaceutically acceptable (or pharmacologically acceptable)—refers to molecular entities and compositions that do not produce an adverse, allergic or other untoward reaction when administered to an animal or a human, as appropriate.

Pharmaceutically acceptable carrier—includes any and all solvents, dispersion media, coatings, antibacterial, isotonic and absorption delaying agents, buffers, excipients, flavorings, binders, lubricants, gels, surfactants and the like, that may be used as a media for a pharmaceutically acceptable substance.

Unit—a unit of biological activity as determined by exhypoxic polyeythemic mouse bioassay and compared to World Health Organization standards.

Any numerical values recited herein include all values from the lower value to the upper value in increments of one unit provided that there is a separation of at least two units between any lower value and any higher value. As an example, if it is stated that the concentration of a component or value of a process variable such as, for example, osmolality, temperature, pressure, time and the like, is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

A. Preservatives: Phenoxyethanol and Benzethonium Chloride

The preservatives contemplated for use according to the present invention are benzethonium chloride, phenoxyethanol and phenylethyl alcohol, any variants of these preservatives and their structural analogues. It is specifically contemplated that any of these preservatives may be used as the sole preservative in the presently disclosed formulations, or they may advantageously be used in combination with each other. As shown herein, formulations of the present invention using a combination of phenoxyethanol and benzethonium chloride prove to have synergistic effects and are therefore particularly preferable.

Benzethonium chloride, phenoxyethanol and phenylethyl alcohol may be used in the presently disclosed formulations in any effective amount. The total preservative concentration is preferably between about 0.001% and about 4.0% of the total formulation. Particularly advantageous concentrations of total preservative are those maintained as low as possible to achieve the requisite antimicrobial effect, while minimizing the potential for adverse reactions.

In preferred embodiments of the present invention, both benzethonium chloride and phenoxyethanol are used together. Surprisingly, when used together these preservatives have a synergistic effect on one another. To achieve the equivalent antimicrobial effect when used alone, the concentrations of benzethonium chloride or phenoxyethanol must each be greater than the total preservative concentration if they are used in combination and, in general, at least twice as much of the preservative must be used if employed alone. Thus for example, if either benzethonium chloride or phenoxyethanol is used alone, approximately at least twice as much benzethonium chloride or phenoxyethanol will be required to achieve the same effect as an amount of benzethonium chloride in combination with phenoxyethanol. Further, even at these higher concentrations of benzethonium chloride and phenoxyethanol, the individual formulations may not meet United States, European or Japanese antimicrobial regulatory criteria. Preferred combined formulations include benzethonium chloride in concentrations of from about 0.001 to about 0.1% in combination with phenoxyethanol in concentrations of from about 0.01 to about 1.0%. More preferred combined formulations contain benzethonium chloride in a concentration of from about 0.01% to about 0.02% and phenoxyethanol in a concentration of from about 0.25% to about 0.5%.

In another embodiment, the present invention includes benzethonium chloride in combination with phenylethyl alcohol. Preferred formulations include benzethonium chloride in concentrations of from about 0.001 to about 0.1% together with phenylethyl alcohol in concentrations of from about 0.01 to about 1.0%. More preferred formulations contain benzethonium chloride in a concentration of from about 0.15 to about 0.25% and phenylethyl alcohol in a concentration of from about 0.2 to about 0.5%. A most preferred formulation in which benzethonium chloride and phenylethyl alcohol are used in concert, includes benzethonium chloride in a concentration of about 0.02% and phenylethyl alcohol in a concentration of about 0.25%.

B. Active Ingredients

The pharmaceutical formulations comprising preservatives as disclosed herein may be formulated using virtually any active ingredient. In particular, benzethonium chloride and phenoxyethanol have synergistic effects and are useful in multi-dose pharmaceutical formulations comprising the following classes of active ingredients: cardiovascular; chemotherapeutics, gastrointestinal and liver; topical; hematologic; antihistaminics; antimicrobials; antiepileptic or antiseizure agents; sedatives and hypnotics; diuretics; psychopharmacologics; antimigraines; ophthalmics; hormones; proteins or peptides and others as needed.

The skilled worker will recognize which individual agents are useful in multi-dose formulations and can combine those agents with the appropriate amounts of benzethonium chloride, phenoxyethanol and/or phenylethyl alcohol as needed according to the individual formulator's needs or demands of the formulation itself. It should be readily apparent that agents listed in one group or class may be useful in other applications, and that such alternative uses still fall within the scope of the present application. In other words, the classification of agents in this disclosure is not intended to be limiting. Likewise, the use of any active ingredient in combination with any other active ingredient, according to the presently disclosed compositions and methods is contemplated to be within the scope of the present invention.

1. Cardiovascular Agents

Virtually any agent that effects the heart or the blood vessels, directly or indirectly, may be used as a cardiovascular agent and as the active ingredient in the compositions and methods employing benzethonium chloride, alone or in combination with phenoxyethanol or phenylethyl alcohol disclosed herein. Specific classes of useful cardiovascular agents according to the present invention include the following: sympathomimetics; α-adrenergic blocking drugs; β-adrenergic blocking drugs; antimuscarinic drugs; ganglionic blocking agents or other drugs that compete with acetylcholine at postsynaptic nicotinic receptors; digitalis and its related drugs such as coronary and peripheral dilators and antidysrhythmic agents; and ACE inhibitors. Agents affecting parenteral fluids and diuretics may also be used as cardiovascular agents, and are discussed in a separate section herein. Additional agents used in cardiovascular applications that may be employed according to the present invention include antihypertensive and hypotensive agents. Antiadrenergic agents, saluretics, and antihypotensive direct vasodilators are all functional antihypertensive or hypotensive classes of drugs.

Peripheral vasodilators are substances which dilate the arterioles and increase blood flow in the numerous systemic vascular beds, especially the extremities. Thus, centrally acting, reflexly acting or ganglionic blocking drugs that reduce sympathetic tone to the periphery are peripheral vasodilators that may be used in the formulations disclosed herein. Additionally, sympathomimetics with prominent $\beta_2$ receptor stimulant actions are employed for their peripheral vasodilator effects; while adrenergic blocking agents are used as peripheral vasodilators to improve flow through specific vascular beds. Such agents are employed in the treatment of vasospastic disorders such as Raynauds disease, causalgias and reflex dystrophy, vasospasm associated with arterial embolism and thrombophlebitis, immersion foot, trench foot, herpes zoster, decubitus ulcers and degenerative arteriole diseases such as thromboangiitis, obliterans, artherosclerosis obliterans, acrocyanosis and diabetic gangrene. It is specifically contemplated that any agent useful as a peripheral vasodilator is useful in the presently disclosed compositions and methods.

Other cardiovascular agents useful according to the present invention include antianginal agents such as the organo nitrates and the calcium entry blocking agents; antiplatelet agents, such as aspirin and sulfinpyrazone; vasopressor agents such as those having vasoconstrictor or cardiostimulator activity that may be used to elevate blood pressure under appropriate conditions, such as, for example, dopamine; cardiac glycosides, or other agents that act as direct cardiotonic agents on the myocardium to increase the force of contraction, including digitalis, deslanoside, digitoxin, digoxin, and digoxin immune fab; phosphodiesterase inhibitors, also known as inodilators, including amrinone, flosequin, and milrinone lactate; and antidysrhythmic agents such as β-adrenergic blocking drugs, colinergic agents, anticholinesterases and β-agonists, including adenosine, amiodarone hydrochloride, bretylium tosylate, disopyramide phosphate, flecainide acetate, mexiletine hydrochloride, moricizine hydrochloride, procainamide hydrochloride, lidocaine hydrochloride, propafenone hydrochloride, quinidine gluconate, quinidine polygalacturonate, quinidine sulfate, and tocanide hydrochloride.

Additional cardiovascular agents that may be employed in the presently disclosed compositions and methods include calcium channel blockers (CCBs), and other agents, known as calcium entry blockers, calcium antagonists and slow channel blockers, such as verapomil, diltiazem, amlodipine, bepridil hydrochloride, felodipine, isradipine, nicardipine hydrochloride, nifedipine and nimodipine (these agents have also been found to effectively treat central nervous system disorders such as stroke and migraine); agents that effect blood lipids (cardiovascular agents because of the relation of blood lipids to artherosclerosis) including aminosalicylic acid, cholestyramine resin, clofibrate, colestipol hydrochloride, gemfibrozil, lovastatin, pravastatin sodium, probucol, simvastatin, dextrothyroxine sodium, fish oils and omega 3 fatty acids; and special use cardiovascular drugs such as alprostadil.

Any of the above listed agents, or their equivalents or analogs, may be advantageously used in the presently disclosed compositions and methods, used either alone or in combination with one another or any other active agent depending upon the needs of the formulator or intended application.

2. Gastrointestinal and Liver Agents

Agents useful in treating gastrointestinal or liver disorders may be incorporated into pharmaceutical formulations comprising benzethonium chloride, alone or in combination with phenoxyethanol or phenylethyl alcohol as disclosed herein. The major categories of agents used in gastrointestinal or liver applications are antacids; $H_2$-receptor antagonists; $H^+/K^+$ ATPase inhibitors; drugs that enhance mucosal resistance; digestants, including pancreatic enzymes; laxatives; antidiarrheals; emetics; antiemetics; prokinetic agents; and adsorbants. Additional agents used in the treatment of gastrointestinal or liver disorders include immunosuppressive drugs, antiinflammatory drugs, immunostimulants, and antibiotics. Any of these several categories of agents may be used according to the compositions and methods disclosed herein.

Specific antacids that may be used include sodium bicarbonate, calcium carbonate, aluminum hydroxide, magnesium hydroxide; magnesium oxide, magaldrate, magnesium trisilicate and aluminum compounds, such as aluminum carbonate gel or aluminum hydroxide gel. Antacids are commonly used in combination, and it is specifically contemplated that any combination of antacids, or any other mentioned gastrointestinal or liver agents, may be used in the pharmaceutical compositions and methods of the present disclosure.

As stated, other agents used for the treatment of gastrointestinal or liver conditions include $H_2$ receptor antagonists, which are generally histamine analogs, such as burimamide, cimetidine, famotidine, nizatidine, and ranitidine; $H^+/K^+$ ATPase inhibitors such as substituted benzimidazoles and omeprazole; agents that enhance mucosal protection including misoprostil, sucralfate; and digestants such as choleretics (bile, bile acids and bile salts), hydrochloric acid, pancreatic enzymes such as mixtures of lipase, amylase and protease and ursodiol.

Additional gastrointestinal and liver agents used in the treatment of gastrointestinal conditions include laxatives, such as bulk forming laxatives such as those consisting of polysaccharides and cellulose derivatives that are undigestable; emollient laxatives, such as ducosate sodium, or other surfactants which facilitate mixture of water and lipid soluble substances to soften stool, or stimulate water secretion in the gastrointestinal tract; lubricant laxatives, such as mineral oil, which allow easier passage of a stool because of an oil coating, or which inhibit colonic reabsorption of water; saline laxatives such as magnesium citrate and sodium phosphate which exert an osmotic effect that increases the water content in volume of stool; stimulant laxatives, such as bisacodyl, phenolphthaline and cinna, which work by various mechanisms including inhibition of absorption, enhancement of secretion and effects of motility; and hyperosmotic laxatives such as lactulose, which exert an osmotic effect and may have some effect on intestinal motility. Other exemplary laxatives that may be used according to the present disclosure include aloe, castor oil, magnesium sulfate, and sodium phosphate.

Still other exemplary gastrointestinal or liver agents that may be incorporated into the present inventions include: emetics such as apromorphine, morphine, hydrogenated ergot alkaloids, digitalis glycosides, copper sulfate, mustard, sodium chloride, zinc sulfate, and veratrum; and antiemetics from the following six groups: antipsychotics, such as phenothiazines, butyrophenones, or other agents that act at the chemoreceptor trigger zone to block dopaminergic emetic receptors excited by apromorphine; antihistaminics, which provide relief from motion sickness; anticholinergics, often in combination with D-amphetamine and scopolamine effective against motion sickness; cannabinoids, especially useful in the emesis from cancer chemotherapy; 5-$HT_3$-receptor antagonists such as ondansetron, blocking both peripheral and central 5-$HT_3$-receptors and especially effective against the emetogenic effects of chemotherapy; and other agents such as trimethobenzamide, emetoclopramide which block dopamine receptors in the chemoreceptor trigger zone; diphenidol, and scopolamine.

Adsorbants are chemically inert powders that have the ability to adsorb gases, toxins and bacteria. Exemplary adsorbants that may be used as the active ingredient in the presently disclosed pharmaceutical formulations and methods of their use include activated charcoal, kaolin, pectin, bismuth subcarbonate, bismuth subnitrate, magnesium trisilicate. Hepatic immunostimulants also are often used to treat chronic liver diseases such as hepatitis B and hepatitis C. These drugs include interferon-$\alpha$-2B, which is generally a recombinant drug. Again, all of these agents are useful in the present compositions and methods.

Many other drugs with diverse actions on the gastrointestinal tract but that do not fit neatly into the above categories are also used to treat gastrointestinal disorders and may be employed in pharmaceutical formulations as disclosed herein. Such other drugs may include anise oil, anisotropine methylbromide, bismuth subcarbonate, camphor, camphor spirit, caraway, caraway oil, cardamom oil, cardamom seed, cardamom tincture or compound, quinodiol, chlorabutanol, chloroform, lactase, lactulose, and simethicone.

3. Topical Drugs

Chemical agents may be applied to the skin and mucous membranes for localized effects within the skin or membrane or for systemic effects. Such agents may also be referred to as topically active agents, and be used in preserved pharmaceutical formulations, comprising the preservative benzethonium chloride alone, or in combination with either phenoxyethanol or phenylethyl alcohol. Topical agents may be protectives, adsorbents, demulcents, emollients or cleansing agents. They also may be relatively inert, and may have particular value as vehicles and excipients. Additional useful topical agents include astringents, irritants, rubefacients, vesicants, sclerosing agents, caustics, escharotics, many keratolytic (desquamating) agents and a variety of other dermatologicals including hypopigmenting and antipruritic agents.

Protectives are any agents that isolate exposed surfaces of skin or other membranes from harmful or annoying stimuli.

Related agents, adsorbants and demulsants, have primarily a dermatological function. Exemplary protectives and adsorbants that may be used in the present invention include the following: dusting powders such as starch or other carbohydrate powders, including those containing an antiseptic; absorbable dusting powders such as biosorb and ezon; powders containing agents that promote debridement of wounds such as those containing beads of dextranomer; bentonite; bismuth; boric acid; calcium carbonate; cellulose; corn starch; magnesium stearate; talc; titanium dioxide; zinc oxide; zinc stearate; aluminum hydroxide; dimethicone; petrolatum gauze; gelatins; lanolin and related compounds such as kaolin, mineral oils, olive or peanut oils; petrolatum; silicones; and zinc carbonate.

Demulsants are protective agents that are employed primarily to alleviate irritation, particularly of mucous membranes or abraded tissues. Exemplary demulsants that may be used in the disclosed pharmaceutical formulations include acacia, agar, benzoine, carbomer, gelatin, glycerin, glycerin suppositories, glycyrrhiza, hydroxyethyl cellulose, hydroxypropyl cellulose, and hydroxypropyl methyl cellulose. Additional exemplary demulsants include various ophthalmic solutions, such as those comprising hydroxypropyl methyl cellulose, methyl cellulose, polyvinyl alcohol, propylene glycol, sodium alginate, or tragacanth.

Emollients are bland, fatty or oleaginous substances, which may be applied locally, particularly to the skin but also to other mucous membranes. Exemplary emollients amenable to use in the presently disclosed compositions and methods include lanolin, both the hydroxylated and acetylated forms; isopropyl myristate and palmitate; oleyl alcohol; sodium lauryl sulfate; various animal fats and oils such as spermaceti, mineral oils, paraffin, and petrolatum; red petrolatum; vegetable oils, including castor oil, cocoa butter, coconut oil, corn oil, cottonseed oil, olive oil, peanut oil, persic oil, and sesame oil; waxes such as cetylesters wax, cold cream, hydrophilic ointment, rosewater ointment, spermaceti, and white or yellow wax; and various other emollients including glycerin, petrolatum, isopropyl myristate, and myristyl alcohol. Oil extracted from the livers of shark, (i.e., shark liver oil), may also be useful as an emollient.

Astringents include locally applied protein precipitants, which have such a low cell penetrability that the action essentially is limited to cell surface and the interstitial spaces. Astringents are used therapeutically to arrest hemorrhage by coagulating the blood and to check diarrhea, reduce inflammation of mucous membranes, promote healing, toughen the skin or decrease sweating. Astringents may be usefully formulated and employed according to the disclosed compositions and methods. Principal astringents include salts of the cations aluminum, zinc, manganese or bismuth; certain other salts that contain these metals (such as promanganates); and tanins or related polyphenolic compounds. Acids, alcohols, phenols and other substances that precipitate proteins may be astringent in the appropriate amount or concentration.

Antiperspirants and deodorants can be applied as aerosols, spray pads, sticks and roll-on liquids, creams and semisolids for the control of excessive perspiration and body odor. Antiperspirants are designed to decrease the flow and/or inhibit the bacterial degradation of skin secretions. Agents most commonly used as antiperspirants include aluminum chlorohydrates, aluminum chloride, buffered aluminum sulfate and zirconyl chlorohydrates. Exemplary antiperspirants include those aluminum chlorohydrates available in anhydrous or salt formulations that differ in the ratio of aluminum to chlorine, as well as in complexes with polyethylene glycol or polypropylene glycol. Buffered aluminum sulfate (8% aluminum sulfate buffered with 8% sodium aluminum lactate) may also be used. Additional antiperspirants include glutaraldehyde, formaldehyde, methenamine, and scopolamine hydrobromide.

Other topical agents that may be used advantageously according to the disclosed compositions include irritants; rubefacients (agents that induce only hyperemia); vesicants; caustics or corrosives and escharotics; keratolytics (desquarnating agents); and cleansing preparations, such as soaps, shampoos or detergents, may also be used according to the present invention.

4. Hematologic Agents

Hematologic agents are any agents affecting the blood, body fluids and electrolyte balances. These also may also be used as the active ingredient in pharmaceutical formulations containing benzethonium chloride, alone or in combination with phenoxyethanol. Exemplary hematologic agents include plasma extenders, such as dextran 40, dextran 70, and dextran 75; antibodies and isoagglutinins, including blood grouping and typing serums such as anti-A, anti-B, and anti-Rh blood-grouping serums, immune globulins, and immune sera; blood clotting proteins such as antihemophilic factor, cryoprecipitated antihemophilic factor, antithrombin III, antiinhibitor coagulant complex, and factor IX complex.

Additional exemplary hematologic agents include anticoagulants or other agents which delay blood coagulation, including those which fall into three general types of anticoagulants: calcium sequestering agents, heparin and heparin substitutes and prothrombopenic anticoagulants (oral anticoagulants). Exemplary anticoagulants include ditumarol, anisindione, warfarin sodium, various citrate dextrose solutions or sodium citrate solutions, heparin calcium, heparin low molecular weight, heparin sodium, dihydroergotamine mesylate, potassium oxalate, sodium citrate, and sodium oxylate. Exemplary thrombolytic agents include streptokinase, urokinase, anisoylated plasminogen-streptokinase activator complex (APSAC), prourokinase (Pro-UK), tissue plasminogen activator (TPA), recombinant forms of these, anistreplase, and alteplase (recombinant). Exemplary antiplatelet agents include aspirin, ticlopidine hydrochloride, dipyridamole, calcium channel blockers, β-adrenergic, and anagrelide. All of these agents may be employed according to the presently disclosed formulations and methods.

Anticoagulant antagonists may also be used as hematologic agents in the disclosed compositions and methods. Exemplary anticoagulant antagonists include vitamin K or its synthetic substitutes, menadiol sodium diphosphate, menadione, menadione sodium bisulfite, phytonadione, protamine sulfate. Fibrinolysin inhibitors such as aminocaproic acid, tranexamic acid; hemostatics and styptics such as alum, cellulose, collagen, absorbable gelatin powder or gelatin sponge, and thrombin; electrolytes and systemic buffers such as ammonium chloride, calcium carbonate, calcium chloride, calcium citrate, calcium glubionate, calcium gluceptate, calcium gluconate, calcium glycerophosphate, calcium lactate, calcium levulinate, dibasic calcium phosphate, tribasic calcium phosphate, magnesium sulfate injection, potassium acetate, potassium chloride, potassium gluconate, potassium mixtures, potassium phosphates, mono- and di-potassium phosphates, potassium and sodium phosphates, sodium acetate, sodium bicarbonate, sodium chloride, sodium citrate and citric acid solution, sodium lactate injection, monobasic sodium phosphate, and tromethamine; and cation complexing agents such as cellulose sodium phosphate, deferoxamine mesylate, dimercaprol, edetate calcium disodium, penicillamine, sodium polystyrene sulfonate, succimer, trientine hydrochloride may also be used.

Finally, additional hematologic agents such as hematopoietics and other agents affecting blood production are useful according to the present invention. Hematopoietics are antianemics that aid in the production of red and white blood cells. Hematinics are antianemics that increase the hemoglobin content of blood through erythropoiesis or through an increase in hemoglobin content of erythrocytes. Useful hematopoietics include: iron and iron compounds such as ascorbic acid, ferrous fumarate, ferrous gluconate, ferrous sulfate, iron dextran injection, and polyferose; hematopoietic growth factors such as epoetin-α, filgrastim, sargramostin, and other agents that regulate the proliferation and differentiation of progenitor stem cells found in the bone marrow; antihematopoietic agents, such as hemin, methylene blue, pentoxifylline, sodium nitrate, and other agents facilitating the management of an increase in the number of circulating erythrocytes.

5. Antihistamines

Antihistamines, of a variety of classes, are useful as the active agent in pharmaceutical formulations containing benzethonium chloride alone, or in combination with either phenoxyethanol or phenylethyl alcohol. Specific exemplary classes of antihistamines that are useful in the disclosed compositions and methods include ethanolamines, ethylene diamines, alkylamines, phenothiavines, and piperidines.

Antihistamines generally are sedating and display an anticholinergic activity. Antihistamines particularly useful in the present invention include those that are $H_1$-receptor antagonists, and act by competitively antagonizing the effects of histamine at receptor sites. They generally do not block the release of histamine, and, hence, offer only palliative relief of allergic symptoms. Exemplary antihistamines useful according to the present invention include: astemizole, brompheniramine maleate, carboxamine maleate, chlorpheniramine maleate, clemastine fumarate, cyproheptadine hydrochloride, cyclizine, dexbrompheniramine maleate, dexchlorpheniramine maleate, diphenhydramine hydrochloride, dimenhydrinate, diphenylpyraline hydrochloride, doxylamine succinate, hydroxyzine hydrochloride, meclizine, methdilazine, methdilazine hydrochloride, phenindamine tartrate, promethazine hydrochloride, pyrilamine maleate, terfenadine, fexofenadine, theophyline, trimeprazine tartrate, tripelennamine citrate, trefalinamine hydrochloride, and triproladine hydrochloride.

Also contemplated to be useful are inhibitors of histamine release, such as chromalyn sodium; seratonin antagonists such as azatadine maleate, and cyproheptadine hydrochloride. Any of the above classes of compounds, as well as those individually listed, may be used alone or in combination in pharmaceutical formulations containing one or more of the preservatives benzethonium chloride, phenoxyethanol, or phenylethyl alcohol.

6. Antibiotics

A broad range of antibacterial agents may be used as the active ingredient in the pharmaceutical formulations and methods disclosed herein. Systemic antibacterial agents that may be used in the presently disclosed pharmaceutical formulations preserved with benzethonium chloride alone, or in combination with either phenoxyethanol or phenylethyl alcohol, include sulfonamides, such as sulfabenzamide, sulfadiazine and sulfamethazine; antibiotics such as penicillin, or other β-lactam antibiotics such as amoxycillin, ampycillin, carbenicillin disodium; cephalosporins, such as cefadroxil, cefaclor, and cefixime; carbapenems and monobactams, such as aztreonam and imipenem; β lactamase inhibitors, such as sulbactam sodium; aminoglycosides, such as gentamicin sulfate, kanamycin sulfate, neomycin sulfate and tobramycin; macrolides, such as azithromycin, erythromycin, and spiramycin; polypeptides, such as bacitracin, capreomycin sulfate, and vancomycin; tetracyclines, such as doxycycline, and tetracycline hydrochloride; and fluoroquinolones, such as norfloxacin and ciprofloxacin hydrochloride. Additionally, various other miscellaneous antibiotics are also useful according to the present disclosure. Exemplary miscellaneous antibiotics that may be used include amphotericin-B, cycloserine, and vancomycin hydrochloride. Additionally, various other antimilarial, antiprotozoal and antifungal, and antiviral agents such as interferons, methisazone, and other antiviral substances, are useful in the disclosed compositions and methods.

7. Antiepileptic and Anti-seizure Agents

Agents used for the treatment of seizure disorders may be employed as the active agent in pharmaceutical formulations containing benzethonium chloride alone or in combination with phenoxyethanol or phenylethyl alcohol. Exemplary anti-seizure agents that may be used in this fashion include: phenytoin, carbamazepine, acetazolamide, chloropromazine hydrochloride, clonazepam, diazepam, dilantin, dimenhydrinate, diphenhydramine hydrochloride, ephedrine sulfate, divalproex sodium, ethosuximide, ethotoin BP, felbamate, magnesium sulfate, mephenyloin, mephobarbital, paramethadione, phenobarbital sodium, phenyloin sodium, primidone, sodium bromide, trimethadione, substituted dibenzoxazepines and valproate sodium. In addition to these specifically listed exemplary anti-seizure medications, any other agent used as an anti-seizure, antiepileptic or anticonvulsant agent is specifically contemplated to be useful according to the pharmaceutical formulations disclosed herein.

8. Sedatives and Hypnotics

Agents that have the effect of a sedative or the effect of inducing relaxation and rest but not necessarily sleep, in addition to any hypnotic agent which induces sleep, may be used as the active agent in the presently disclosed pharmaceutical formulations and methods. Generally, agents of these types have the ability to induce a nonselective, reversible depression of the central nervous system. Sedatives and hypnotics may be divided into three groups: benzodiazepines, barbiturates, and other miscellaneous sedative and hypnotic agents. Any of these groups may be useful in the disclosed formulations. Specific examples of these types of agents include buclizine, diphenhydramine, benzodiazepine, methotrimeprazine, scopolamine, diazepam, flurazepam, lorazepam, pentobarbital, meprobamate, phenobarbital, chlorhydrate, chlormezanone, and methyprylon. Alternate and additional exemplary sedative and hypnotic agents include, generally, inorganic salts such as bromides; chloro derivatives such as chlorohydrate; acetylenic alcohols such as ethchlorvynol; cyclic ethers such as peraldehyde; carbamic acid esters of alcohols; carbamic acid esters of glycols; diureides such as barbiturates; piperidinedione derivatives such as glutethimide; disubstituted quinazolones such as methaqualone; and miscellaneous aromatic tertiary alkylamines such as antihistaminics and parasympatholytics.

9. Diuretics

Diuretics are agents that reduce the volume of extracellular fluid, enhance the urinary excretion of sodium chloride and, secondarily, increase the volume of urine excreted by the kidneys. Virtually any substance that has these effects may be classified as a diuretic and may be useful as the active agent in the pharmaceutical formulations and methods disclosed herein. Most diuretic agents block sodium and/or chloride reabsorption in the renal tubules. Broadly, diuretics may be separated into the following groups: osmotics, carbonic and anhydrase inhibitors, thiazides, potassium-sparing diuretics such as spironolactone, triamterene and amiloride, looped or high ceiling diuretics. Exemplary osmotic diuretics include glycerin, mannitol, isosorbide, and urea.

Exemplary renal tubular-inhibiting diuretics include carbonic anhydrase inhibitors such as acetazolamide, steroacetazolamide sodium, dichlorphenamide, methazolamide, mersalyl with theophylline. Additional exemplary useful renal tubular inhibiting diuretics include the benzothiadiazine and related diuretics, such as bendroflumethiazide, benzthiazide, chlorothiazide, chlorothalidone, cyclothiazide, flumethiazide, hydrochlorothiazide, indapamide, metolazone, polythiazide, and quinethazone, aminophylline, caffeine, theobromine, and probenecid.

Exemplary potassium-sparing diuretics may include spironolactone, triamterene, amiloride, amiloride hydrochloride. Exemplary loop diuretics include ethacrynic acid, furosemide and bumetanide. Additionally, as with all groups of agents, any combination of any of the above-listed diuretics may also be used as active agents in the disclosed pharmaceutical formulations, and are specifically contemplated to be within their scope.

10. Psychopharmacologic Agents

Psychopharmacologic agents, alternatively referred to as psychoactive or psychotropic agents, are used widely in the treatment of behavioral disorders and mental disorders, such as anxiety, delusions, hallucinations, paranoid states, catatonia, social withdrawal, and autonomic nervous system dysfunctions. Psychopharmacological agents may be divided into the following groups: antipsychotics, antianxiety agents, antidepressants, psychogenic agents. Agents in all of these groups may be useful in the presently disclosed pharmaceutical formulations and disclosed methods.

Exemplary useful antipsychotic agents include antipsychotic agents classified in any of the following six groups: phenothiazines, such as chlorpromazine; thioxanthenes, such as chlorprothixene and thiothixene; butyrophenones such as haloperidol; dihydroindolone derivatives such as molindone; dibenzoxazepines such as loxapine; and dibenzodiazepines such as clozapine. Exemplary antianxiety agents, or other agents that have sedative and antianxiety applications include various antihistaminics such as diphenhydramine; acetylenic carbinols, such as ethchlorvynol; monoureides such as carbromal; barbiturates such as phenobarbital; piperidinediones such as methylprylon; propyl alcohol derivatives such as meprobamate; and benzodiazepines such as chlordiazepoxide.

Exemplary antidepressants that may be used in the presently disclosed compositions and methods include any agents that relieve the symptoms of major depressive disorders and may result in an increased output of behavior. Specific exemplary anti-depressants include those that may be classified as tricyclic antidepressants such as imipramine hydrochloride, imipramine pamoate, amitriptyline hydrochloride, amoxapine, desipramine hydrochloride, doxepin, protriptyline hydrochloride and trimipramine. Alternative exemplary antidepressants may be classified as monoamine oxidase inhibitors such as isocarboxazid, phenelzine sulfate and tranylcypromine sulfate. Still other exemplary antidepressants include second generation antidepressants such as amoxapine, maprotaline, trazodone, fluoxetine and buproprion.

Psychogenic agents are other agents that induce temporary abnormalities of the mental state of human subjects or the behavior of animals. They too may be useful in the presently disclosed pharmaceutical formulations, and include, for example, cannabis, lysergic acid diethylamide, and mescaline.

11. Antimigraine Agents

Various agents that function to counteract cerebral vasodilation associated with migraine may be used in the treatment of migraine, and may be employed as the active agent in the pharmaceutical formulations disclosed herein. Exemplary antimigraine medications include ergot alkaloids, various ergotamines, and sumatriptan succinate.

Often related to the agents that are used to treat migraine medicine, are agents used to stimulate smooth muscle of the uterus known as oxytocics. These agents may also be useful as the active agents in the disclosed pharmaceutical formulations. Exemplary useful oxytocics include carboprost tromethamine, cyproheptadine, dinoprostone, methylergonovine maleate, methysergide maleate, oxytocin, and sodium chloride.

12. Hormones

Hormones, or any other agents secreted by the endocrine or ductless glands and nonglandular tissues which serve to integrate metabolic processes may be useful as the active ingredient in the disclosed pharmaceutical formulations and methods. Hormones may be amino acid derivatives, steroids, or a variety of other diverse substances. Exemplary hormones that may be used according to the disclosed methods and compositions include sematropins including growth hormones; gonadotropic hormones, such as follicle-stimulating hormone, or luteinizing hormone; prolactin; thyrotropic hormones; adrenal corticotropic hormone; or virtually any other pituitary hormone. Additional exemplary hormones that are useful in the disclosed formulations and methods include human chorionic gonadotropin; corticotropin; and bromocriptine. Additional useful hormones include those from the intermediate lobe such as intermedin, or melanocyte-stimulating hormone; posterior pituitary hormones including oxytocin and vasopressin.

The adrenal hormones may also be useful in the disclosed formulations and methods. Exemplary adrenal hormones include adrenal corticosteroids such as cortisone and cortisone acetate, dexamethasone, hydrocortisone, prednisone and various forms of prednisolone. Also useful are glyburide; parathyroid hormones such as calcitriol and dihydrotachysterol; and pancreatic hormones such as insulin and glucagon, in any of their forms. The thyroid hormones include agents that modulate energy metabolism and certain nonenergetic functions of the body. Useful thyroid hormones include calcitonin, thyroglobulin, and thyroid.

Additional hormones that may be used include the sex hormones which may be classified as estrogenic hormones, progestational hormones, and androgenic hormones. Both estrogenic hormones and progestational hormones are known collectively as ovarian hormones. They may be employed in synthetic as well as natural versions. Exemplary ovarian hormones include estradiol, and various forms of estradiol, estrone, and quinestrol. Exemplary synthetic estrogens include dienestrol, mestranol and norethindrone. A second type of ovarian hormone is progesterone. Exemplary progesterones include ethynodiol diacetate and norethindrone. Related to these drugs are agents, which have the effect of suppressing the effects of estrogen, by a variety of mechanisms. Such agents may also be useful as the active ingredient in the presently disclosed formulation and include, for example, clomiphene citrate and tamoxifen citrate.

Androgenic hormones are those produced generally in the testes. Exemplary useful androgenic hormones include testosterone, cyproterone acetate, danazol, finasteride, oxymetholone, testolactone, and various testosterone analogs and derivative such as testosterone cypionate, testosterone enanthate and testosterone propionate.

13. Proteins or Peptides

Various proteins or peptides may be useful as the active ingredient in the currently disclosed pharmaceutical formulations. It is one advantage of the use of the preservative benzethonium chloride, alone or in combination with phenoxyethanol or phenylethyl alcohol, that they are particularly compatible with peptides and proteins in solution including both recombinant and gene-activated forms of proteins. Exemplary proteins that may be used include many that have been mentioned previously such as erythropoietin, insulin, granulocyte colony stimulating factor (GCSF), hormones, enzymes, vaccines and steroids.

14. Anti-neoplastic Agents

Anti-neoplastic agents, or even combinations of anti-neoplastic agents may be formulated into multidose compositions with benzethonium chloride and phenoxyethanol. Such anti-neoplastic agents which may be used in such formulations, either alone or in combination include, without limitation, tamoxifen, taxotere, doxorubicin, cisplatin, cyclophosphamide, an interferon, a tumor necrosis factor, methotrexate or variants of these agents.

C. Other Composition Components

Optimal disclosed compositions and methods will vary according to factors such as the active ingredient or ingredients, amount of time the formulation will be stored, conditions under which it will be stored and used, including the dosage form of the composition, and the particular patient population to which it may be administered. Adjustments to the formulation by adjusting constituents of the formulations and their relative concentrations, including the amounts of benzethonium chloride, phenoxyethanol and phenylethyl alcohol, may be made as needed according to the needs of the formulator, administrator or patient. Additional constituent elements of the multi-dose formulations of the present invention may include water, a buffer, a pH-adjusting agent, a surfactant or anti-adsorbant, a wetting agent, a gelling agent, a drying agent, an osmolality adjusting agent, or virtually any other additive or carrier, depending upon the desired dosage form.

Formulation characteristics that may be modified include, for example, the pH and the osmolality. For example, it may be desired to achieve a formulation that has a pH and osmolality similar to that of human blood or tissues to facilitate the formulation's effectiveness when administered parenterally. Alternatively, to promote the effectiveness of the disclosed compositions when administered via other administration routes, alternative characteristics may be modified.

Buffers are useful in the present invention for, among other purposes, manipulation of the total pH of the pharmaceutical formulation (especially desired for parenteral administration). A variety of buffers known in the art may be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present invention include sodium or potassium buffers, particularly sodium phosphate. In a preferred embodiment for parenteral dosing, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present invention include a pH of about 2.0 to a pH of about 12.0.

It may also be advantageous to employ surfactants in the presently disclosed formulations. Surfactants or anti-adsorbants that prove useful include polyoxyethylenesorbitans, polyoxyethylenesorbitan monolaurate, polysorbate-20, such as Tween-20™, polysorbate-80, hydroxycellulose, and genapol. By way of example, when any surfactant is employed in the present invention to produce a parenterally administrable composition, it is advantageous to use it in a concentration of about 0.01 to about 0.5 mg/ml.

Additional useful additives are readily determined by those of skill in the art, according to particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 300 Osm/kg and achievable by the use of sodium chloride in concentrations of about 6.5 to about 7.5 mg/ml with a sodium chloride concentration of about 7.0 mg/ml being particularly effective.

D. Preparation of the Compositions

The formulations described herein may be prepared in water suitably mixed with a surfactant, such as hydroxypropylcellulose or polyoxyethylenesorbitans. In many cases, it will be preferable to include isotonic agents, for example, sugars or sodium chloride as described above. Prolonged absorption of the injectable compositions can be brought about by the use in the compositions of agents delaying absorption, for example, aluminum monostearate or gelatin. The disclosed formulations do not require high levels of additional alcohols in order to achieve or maintain their anti-microbial effect. For example, a composition with an alcohol level greater than 55% or greater than 75% or even greater than 90% is not necessary. Other agents that may be employed include, but are not limited to lecithin, urea, ethylene oxide, propylene oxide, hydroxypropylcellulose, methylcelluylose, or polyethylene glycol.

Aqueous compositions (inocula) as described herein may include an effective amount of a desired pharmacologically active agent dissolved or dispersed in a pharmaceutically acceptable aqueous medium. Such compositions are also referred to as inocula. The use of pharmaceutically acceptable carrier media and agents for pharmaceutically active substances is well known in the art. Except insofar as any conventional media or agent is incompatible with the active ingredient, its use in the therapeutic compositions is contemplated. Supplementary active ingredients also can be incorporated into the compositions as described above.

A proteoglycan such as erythropoietin may be formulated into a composition in a neutral or salt form. Pharmaceutically acceptable salts include the acid addition salts (formed with the free amino groups of the protein) and those that are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The therapeutic compositions of the present invention are advantageously administered in the form of injectable compositions either as liquid solutions or suspensions; solid forms suitable for solution in, or suspension in, liquid prior to injection may also be prepared. Alternatively, the compositions of the present invention may be administered as inhalants in an aerosolized form. Depending upon the needs of the formulator, administrator, or the subject of the treatment, the presently disclosed compositions may take virtually any form including liquid, suspension, emulsion, solution, oil, mixture, cream, ointment, gel, suppository, semisolid, aerosol, powder, tablet, or capsule. A typical composition comprises a pharmaceutically acceptable carrier. For instance, the composition may contain 10 mg, 25 mg, 50 mg or up to about 100 mg of human serum albumin per milliliter of phosphate buffered saline.

The formulations as described herein may be contained in a vial, bottle, tube, syringe inhaler or other container for single or multiple administrations. Such containers may be made of glass or a polymer material such as polypropylene, polyethylene, or polyvinylchloride, for example. Preferred containers may include a seal, or other closure system, such as a rubber stopper that may be penetrated by a needle in order to withdraw a single dose and then re-seal upon removal of the needle. All such containers for injectable liquids, lyophilized formulations, reconstituted lyophilized formulations or reconstitutable powders for injection known in the art or for the administration of aerosolized compositions are contemplated for use in the presently disclosed compositions and methods.

EXAMPLES

One skilled in the art will recognize that many formulations or compositions comprising the preservative benzethonium chloride alone, or in synergistic combination with phenoxyethanol, or in combination with phenyl ethyl alcohol, may be prepared. Following is just one example of such a formulation or composition. This example is intended to be illustrative only and is not intended to limit the scope of the invention.

Example 1

An effective antihistaminic composition may be formulated as follows: An effective amount of fexofenadine; xylitol; sorbitol; glycerin; sodium saccharin; benzethonium chloride in a concentration of about 0.005%; phenoxyethanol in an amount of 0.25%, and sodium hydroxide, to adjust the pH.

REFERENCES

U.S. Pat. No. 4,806,524 to Kawagachi et al.
U.S. Pat. No. 5,503,827 to Woog et al.
U.S. Pat. No. 5,661,125 to Stricklan et al.
Handbook of Pharmaceutical Excipients, second edition, 1994.
L. A. Trissel, "Handbook on Injectible Drugs." Ed. 8, American Society of Hospital Pharmacists, Inc. 1994.
Physicians' Desk Reference, ed. 48, 1994.
Physicians' Desk Reference, ed. 50, 1996.
Sandeep Nema, R. J. Washkuhn, and R. J. Brendel, "Excipients and Their Use in Injectable Products," *PDA Journal of Pharmaceutical Sciences & Technology*, Vol. 51(4), July–August 1997.

What is claimed is:

1. A pharmaceutical composition comprising a pharmacologically active ingredient and an amount of benzethonium chloride and an amount of phenoxyethanol wherein the amounts of benzethonium chloride and phenoxyethanol are effective to inhibit microbial growth, and wherein said composition is formulated for administration parenterally, by suppository, or orally by powder, tablet or capsule.

2. The composition of claim 1, further defined as comprising benzethonium chloride in a concentration of from about 0.001 to about 1.0%, and phenoxyethanol in a concentration of from about 0.01 to about 2.0%.

3. A pharmaceutical composition comprising a pharmacologically active ingredient, an amount of benzethonium chloride and an amount of phenoxyethanol, wherein the amounts of benzethonium chloride and phenoxyethanol are effective to inhibit microbial growth, and wherein the benzethonium chloride is present in a concentration of from about 0.001 to about 0.005%, and the phenoxyethanol is present in a concentration of from about 0.01 to about 0.25% and wherein said composition is formulated for administration parenterally, by suppository, or orally by powder, tablet or capsule.

4. The composition of claim 1, 2, or 3, wherein said pharmacologically active ingredient is a cardiovascular agent.

5. The composition of claim 4, wherein said cardiovascular agent is diltiazem, digoxin, dopamine, digitalis, procainamide hydrochloride, lidocaine, verapomil, or levostatin.

6. The composition of claim 1, 2, or 3, wherein said pharmacologically active ingredient is an agent for the treatment of the gastrointestinal system or liver.

7. The composition of claim 6, wherein said agent for the treatment of the gastrointestinal system or the liver is an antacid, a digestant or an emetic.

8. The composition of claim 6, wherein said agent for the treatment of the gastrointestinal system or the liver is lipase, furosamide, morphine, scopolamine, or ranitidine.

9. The composition of claim 1, 2, or 3, wherein said pharmacologically active agent is a hematologic agent.

10. The composition of claim 9, wherein said hematologic agent is heparin, streptokinase, urokinase, tissue plasminogen activator, or aspirin.

11. The composition of claim 1, 2, or 3, wherein said pharmacologically active agent is an antihistamine.

12. The composition of claim 11, wherein said antihistamine is theophylline, diphenhydramine, hydroxyzine or fexofenadine.

13. The composition of claim 11, wherein said antihistamine is fexofenadine.

14. The composition of claim 13, comprising about 0.005% benzethonium chloride, and about 0.25% phenoxyethanol.

15. The composition of claim 1, 2, or 3, wherein said pharmacologically active ingredient is an antimicrobial.

16. The composition of claim 15, wherein said antimicrobial is penicillin, amoxycillin, kanamycin, neomycin, erythromycin, tetracycline, doxycycline, norfloxacin, or cyclosporin.

17. The composition of claim 1, 2, or 3, wherein said pharmacologically active agent is an antiepileptic or anti-seizure agent.

18. The composition of claim 17, wherein said antiepileptic or anti-seizure agent is phenytoin, dilantin, or phenobarbital.

19. The composition of claim 1, 2, or 3, wherein said pharmacologically active agent is a sedative or hypnotic.

20. The composition of claim 19, wherein said sedative or hypnotic is scopolomine, fexofenadine, or methaqualone.

21. The composition of claim 1, 2, or 3, wherein said pharmacologically active agent is a diuretic.

22. The composition of claim 21, wherein said diuretic is furosemide, amiloride, aminophylline, or theobromide.

23. The composition of claim 1, 2, or 3, wherein said pharmacologically active ingredient is a psychopharmacologic agent.

24. The composition of claim 23, wherein said psychopharmacologic agent is an anti-psychotic or an antidepressant.

25. The composition of claim 1, 2, or 3, wherein said pharmacologically active ingredient is an anti-migraine agent.

26. The composition of claim 1, 2, or 3, wherein said pharmacologically active agent is a hormone.

27. The composition of claim 1, 2, or 3, wherein said pharmacologically active agent is a protein or peptide.

28. The composition of claim 1, 2, or 3, further comprising a second active agent.

29. The composition of claim 28, wherein said second active agent is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

30. The composition of claim 1, 2, or 3, wherein said composition is a liquid, suspension, emulsion, solution, mixture, suppository, powder, or tablet.

31. A pharmaceutical carrier composition for use as a carrier of a pharmaceutically active ingredient, wherein said carrier comprises an amount of benzethonium chloride and an amount of phenoxyethanol wherein the amounts of benzethonium chloride and phenoxyethanol are effective to inhibit microbial growth in said composition, and wherein said composition is formulated for administration parenterally, by suppository, or orally by powder, tablet or capsule.

32. The pharmaceutical carrier composition of claim 31, further defined as comprising benzethonium chloride in a concentration of from about 0.001 to about 1.0%, and phenoxyethanol in a concentration of from about 0.01 to about 2.0%.

33. The pharmaceutical carrier composition of claim 31 or 32, wherein said pharmaceutically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

34. A pharmaceutical carrier composition for use as a carrier of a pharmaceutically active ingredient, wherein said carrier comprises an amount of benzethonium chloride and an amount of phenoxyethanol wherein the amounts of benzethonium chloride and phenoxyethanol are effective to inhibit microbial growth in said composition, and wherein the benzethonium chloride is present in a concentration of from about 0.001 to about 0.005%, and the phenoxyethanol is present in a concentration of from about 0.01 to about 0.25% and wherein said composition is formulated for administration parenterally, by suppository, or orally by powder, tablet, or capsule.

35. The pharmaceutical carrier composition of claim 34, wherein said pharmaceutically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

36. A vial for containing multiple dosages of a pharmacologically active ingredient, wherein said vial contains a solution comprising said active ingredient and an amount of benzethonium chloride and an amount of phenoxyethanol wherein the amounts of benzethonium chloride and phenoxyethanol are effective to inhibit microbial growth in said composition, said solution formulated for administration by a route selected from the following: parenteral, suppository, or orally by powder, tablet, or capsule.

37. The vial of claim 36, further defined as comprising benzethonium chloride in a concentration of from about 0.001 to about 1.0%, and phenoxyethanol in a concentration of from about 0.01 to about 2.0%.

38. The vial of claim 36 or 37, wherein said pharmacologically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

39. A pharmaceutical package for containing multiple dosages of a pharmacologically active ingredient, wherein said package contains a solution comprising said active ingredient and an amount of benzethonium chloride and an amount of phenoxyethanol wherein the amounts of benzethonium chloride and phenoxyethanol are effective to inhibit microbial growth in said composition, the benzethonium chloride being present in a concentration of about 0.001% to about 0.07%, and the phenoxyethanol being present in a concentration of about 0.01% to about 0.45%, said solution formulated for administration by a route selected from the following: parenteral, suppository, or orally by powder, tablet or capsule.

40. The pharmaceutical package of claim 39, wherein said pharmacologically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

41. A method of inhibiting microbial growth in a solution comprising a pharmacologically active ingredient, said method comprising adding benzethonium chloride and phenoxyethanol to said solution wherein said solution is formulated for administration parenterally, by suppository, or orally by powder, tablet, or capsule.

42. The method of claim 41, wherein benzethonium chloride is added in a concentration of from about 0.001 to about 1.0%, and phenoxyethanol is added in a concentration of from about 0.01 to about 2.0%.

43. The method of claim 41 or 42, wherein said pharmacologically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

44. A method of inhibiting microbial growth in a solution comprising a pharmacologically active ingredient, said method comprising adding benzethonium chloride and phenoxyethanol to said solution, wherein the benzethonium chloride is added to be in a concentration of from about 0.001 to about 0.005%, and the phenoxyethanol is added to be in a concentration of from about 0.01 to about 0.25% and wherein said composition is formulated for administration parenterally, by suppository, or orally by powder, tablet, or capsule.

45. The method of claim 44, wherein said pharmacologically active ingredient is a cardiovascular agent, an agent for the treatment of gastrointestinal disorders, a hematologic agent, an antihistamine, an antimicrobial, an antiepileptic, an anti-seizure agent, a sedative, a hypnotic, a diuretic, a psychopharmacologic agent, an anti-migraine agent, a hormone, a protein or a peptide.

* * * * *